Figure 3:
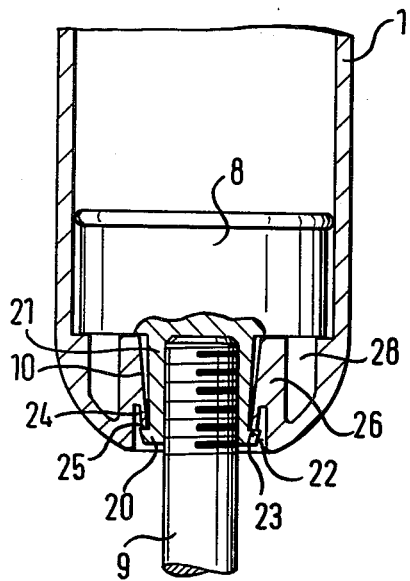

United States Patent [19]

Sarstedt

[11] Patent Number: 4,459,997
[45] Date of Patent: Jul. 17, 1984

[54] BLOOD EXTRACTING AND CENTRIFUGING DEVICE

[75] Inventor: Walter Sarstedt, Nümbrecht, Fed. Rep. of Germany

[73] Assignee: Walter Sarstedt Kunststoff-Spritzgusswerk, Fed. Rep. of Germany

[21] Appl. No.: 321,827

[22] Filed: Nov. 16, 1981

[51] Int. Cl.³ .............................................. A61B 5/00
[52] U.S. Cl. .................................... 128/764; 128/765; 604/110; 604/228
[58] Field of Search ............... 128/763, 765, 766, 764; 604/201, 206, 205, 110, 228, 222, 111, 220, 187, 218, 159; 494/16; 222/386; 210/DIG. 24, 516, 518

[56] References Cited

U.S. PATENT DOCUMENTS

| | | | |
|---|---|---|---|
| 3,115,135 | 12/1963 | Sarnoff | 604/228 |
| 3,262,449 | 7/1966 | Pannier, Jr. et al. | 604/159 |
| 3,438,373 | 4/1969 | Pannier, Jr. | 604/159 |
| 3,577,980 | 5/1971 | Cohen | 604/220 |
| 3,828,778 | 8/1974 | Weinhart | 604/228 |
| 3,937,211 | 2/1976 | Merten | 128/765 |
| 3,985,122 | 10/1976 | Topham | 128/765 |
| 4,057,050 | 11/1977 | Sarstedt | 604/228 |
| 4,066,067 | 1/1978 | Micheli | 128/764 |
| 4,180,069 | 12/1979 | Walters | 604/228 |
| 4,268,481 | 5/1981 | Suovaniemi et al. | 128/765 |
| 4,286,640 | 9/1981 | Knox et al. | 604/111 |

FOREIGN PATENT DOCUMENTS

| | | | |
|---|---|---|---|
| 44211 | 8/1888 | Fed. Rep. of Germany | 604/228 |
| 1956953 | 6/1970 | Fed. Rep. of Germany | 128/765 |
| 2456561 | 11/1977 | Fed. Rep. of Germany | . |

Primary Examiner—Richard J. Apley
Assistant Examiner—Harry J. Macey
Attorney, Agent, or Firm—Townsend and Townsend

[57] ABSTRACT

A blood extracting and centrifuging device has a cylindrical body 1 with front and rear ends 2, 3. The front end is adapted to receive a removable cannula 4 and a piston 8 is sealingly movable within the cylindrical body 1. A piston rod 9 attached to the piston 8 extends through a bore 10 at the rear end of the cylindrical body and is used to retract the piston, from an advanced position adjacent the front end to a retracted position adjacent the rear end, whereby to generate a vacuum in the cylindrical body 1 for extracting blood via the cannula 4. Securing means in the form of an annular retaining projection 22 on one of the piston 8 and the piston rod and an annular lip 24 at the rear end of the cylindrical body 1 are provided to secure the piston to the cylindrical body in its retracted position. After a blood sample has been taken the piston rod 9 can be removed and the cylindrical body 1 inserted directly in a centrifuge without the need to transfer the blood to a centrifuging vessel.

16 Claims, 8 Drawing Figures

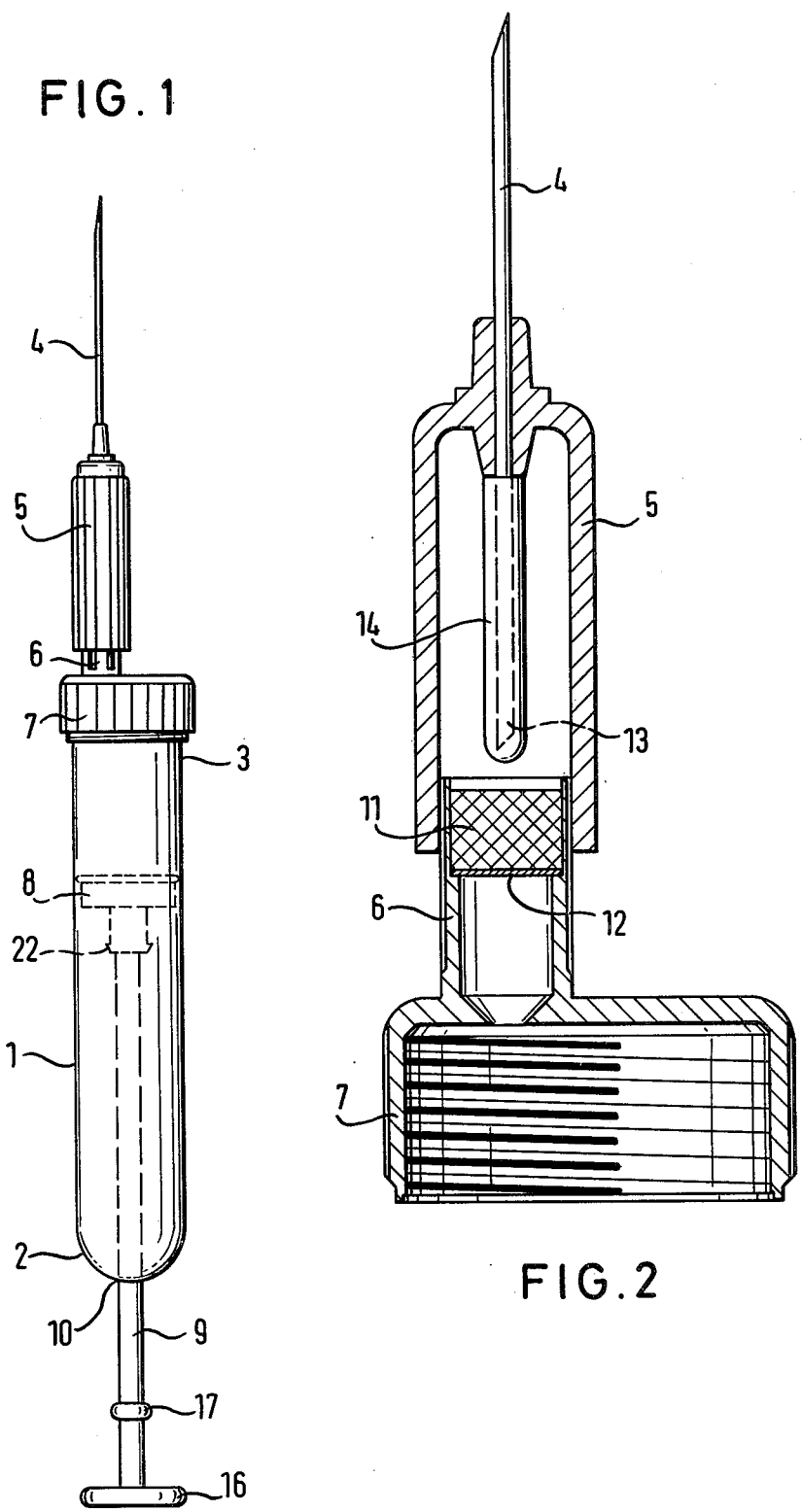

BLOOD EXTRACTING AND CENTRIFUGING DEVICE

The present invention relates to a blood extracting and centrifuging device and has particular reference to a blood extracting device which can be used to extract a sample of blood from a patient's vein and subsequently inserted into a centrifuge to separate the blood serum from the blood corpuscles.

Devices of this kind are known and offer the significant advantage that there is no need to transfer the blood from the blood extraction device to a special sample tube for centrifuging purposes so that handling is facilitated and the operator is protected to a large degree from contact with possibly infectious blood.

Blood extracting and centrifuging devices of this kind tend to fall into two classes.

The devices of the first class, an example of which is shown in German Auslegeschrift No. 18 12 742, basically consist of a preevacuated cylindrical tube which has a permanently sealed rear end and a puncturable seal at its front end. A double ended cannula can be mounted on the front end of the tube and the device is operated in the following manner. The front end of the cannula is first inserted into a patient's vein. The cylindrical tube is then moved telescopically within a sleeve provided on the double ended cannula so that the second end of the cannula punctures the seal or bung whereupon the vacuum in the cylindrical tube sucks blood from the patient's vein through the cannula into the cylindrical tube. It will be appreciated that the cylindrical tube can then be readily inserted into a centrifuge to allow separation of the blood serum from the blood corpuscles. This class of device suffers however from a number of disadvantages. In the first place it is difficult to ensure that the cylindrical tubes remain evacuated particularly when stored for long periods of time. The operator has no real way of knowing whether or not the vacuum is still present within the cylindrical tube with the result that the cannula can be introduced into the vein of a patient before it becomes apparent that the cylindrical tube has lost its vacuum so that the blood extraction procedure must be repeated. This generally proves disturbing and inconvenient for both the patient and the doctor. Furthermore, in young children or older patients there is the significant danger that the sudden application of vacuum to the vein through the cannula will collapse the vein thus preventing the extraction of blood. This is clearly undesirable and may result in several attempts having to be made to obtain a sample of blood, which is clearly unsatisfactory.

For these reasons there has been a move towards a second class of device such as is shown by U.S. Pat. No. 4,057,050. In this second class of device the cylindrical tube is provided with a piston to which is attached a piston rod which extends through a guide bore at the rear end of the cylindrical tube. With this class of device the cannula is introduced into the vein of a patient and the piston is slowly withdrawn to create a vacuum which progressively removes blood from the patient's vein. Using this technique the level of vacuum in the tube can be carefully controlled so that collapse of the patient's vein is avoided. The operation can also be automated by mounting an automatic piston extraction device on the cylinder which allows the rate of extraction of the piston to be carefully controlled. Once the cylindrical tube is full of blood and the piston is located at the rear end thereof the piston rod can be unscrewed from the piston so that the cylindrical tube can be inserted directly into a centrifuge.

This system is clearly very attractive because it can be used with any patient and because there is no danger of loss of vacuum. Unfortunately the presence of a piston gives rise to a number of complications. Clearly a seal is required between the piston and the end of the cylindrical tube in order to prevent loss of blood. It is also convenient for the piston to be physically retained at the rear end of the cylindrical tube. In the arrangements disclosed in U.S. Pat. No. 4,057,050 this is achieved by providing a tapered extension on the piston which seals in a tapered recess at the rear end of the cylindrical tube. As a result of this arrangement an air pocket is inevitably formed between the piston and the end of the tube and this air pocket can give rise to problems during centrifuging. Considerable pressure differences occur at the lip seal of the piston during centrifuging and can result in blood entering the aforementioned air pocket and compressing the air. The piston ceases to be loaded by pressure after the centrifuging operation has been completed and there is the risk that the air which is enclosed in the air pocket, and which is still compressed, will expand resulting in air escaping upwardly past the piston. The air bubbles then enter the blood cake and, in the most unfavourable case, can throw red blood corpuscles from the blood cake into the serum located thereabove, the serum thus being rendered unusable for further examination.

In order to overcome this difficulty the arrangements proposed in U.S. Pat. No. 4,057,050 are provided with a facility for venting this air space. This venting facility takes two forms. In the embodiments in which the piston is sealed at the rear end of the cylindrical tube by mating conical surfaces a number of ribs are provided on the wall of the cylindrical tube adjacent the sealing lip of the piston so that the piston seal is interrupted and the air pocket below the piston can be vented past the piston during centrifuging. In another embodiment of the aforementioned U.S. Pat. No. 4,057,050 the physical connection between the piston and the cylindrical tube is effected by means of an annular locking bead on an extension of the piston, with the locking bead engaging in a ring-shaped recess of complementary semicircular crosssection in a transverse wall at the end of the cylindrical tube. In this embodiment the piston seal with the cylinder remains intact and the air pocket beneath the piston is vented via a groove formed between the locking bead and the locking groove. It will be appreciated that both the above arrangements are relatively complicated. The typical dimensions of a cylindrical tube for a blood extracting device are 9 cm length by 16 mm diameter. These cylindrical tubes are formed by injection molding techniques and clearly the need to provide small vents of a fraction of a millimeter size results in undesirable complication of the injection molding, and adds significantly to the cost thereof.

It would be beneficial if blood extracting devices which are equipped with a piston could also be used in a mode analogous to the first class of blood extracting device. In other words it would be convenient if the piston could first be retracted to generate a vacuum within the cylindrical tube and then physically locked to the rear end of the cylindrical tube prior to the use of the device for extracting blood.

It would in principle be possible to make the locking bead and annular groove arrangement of U.S. Pat. No.

4,057,050 sufficiently strong that the piston of this device could be reliably retained against the vacuum prevailing within the cylindrical tube. This would however then result in a situation in which, when using the movement of the piston to extract blood in the previously described manner, a great deal of force would need to be exerted by the operator to engage the annular bead in the annular groove. This would however be highly undesirable because the resulting jolt could easily cause the cannula to penetrate the opposite wall of the patient's vein.

An alternative way of locking a piston to the rear end of a cylindrical collecting tube as shown in Swiss Pat. No. 497 171. This arrangement, which is not simultaneously suitable for use in a centrifuge, requires a rotary movement of the piston rod relative to the cylindrical tube to effect the aforementioned locking. A similar rotational movement is required for the blood extraction device shown in U.S. Pat. No. 3,937,211.

Rotary locking movements of this kind are however not suitable for use with removable piston rods. If a threaded connection is present between the piston rod and the piston it is possible for the act of locking the piston to the cylindrical tube to result in the undesired release of the threaded connection between the piston rod and the piston. If the piston rod is provided with a weak fracture point then the danger is continuously present that the act of securing the piston to the cylindrical tube will result in a fracture of this weak point, particularly as such weak points are extremely sensitive to torsional loads.

The greatest danger of a threaded connection is however that the manually effected threaded connection is not adequately secured so that the retention of the piston is unreliable. This can lead to the connection of the piston to the cylindrical tube being unintentionally released when the cannula is inserted in the vein with the result that the piston will spring back into the tube under the effects of the vacuum which represents a non-acceptable risk.

It is a principal object of the present invention to provide a blood extraction and centrifuging device having a retractable piston mounted in a generally cylindrical extraction tube in which the piston can be reliably locked to the rear end of the extraction tube with the exertion of only a minimal amount of force on the part of the operator, in which the injection molding is of a simple form which can be easily manufactured and in which no special provision need be made for venting the air pocket beneath the piston.

In order to satisfy this object there is provided a blood extracting and centrifuging device having a cylindrical body with front and rear ends, said front end being adapted to receive a removable cannula, a piston sealingly movable within said cylindrical body, a piston rod removably attached to said piston and extending through a bore at said rear end for moving the piston from an advanced position adjacent said front end to a retracted position adjacent said rear end, whereby to generate a vacuum in said cylindrical body for extracting blood via an attached cannula, and securing means for retaining said piston in said retracted position even after removal of said piston rod, said securing means comprising an annular retaining projection on one of the piston and a front end portion of the piston rod, said retaining projection having a first surface which tapers substantially conically in a rearward direction away from said front end and a second, retaining surface which extends substantially transverse to said piston rod, and wherein said bore is provided with an annular lip adapted to snap into engagement with said annular retaining projection in front of said second, retaining surface, said annular lip having a surface complementary to said second retaining surface and being formed on an annular sleeve defining said bore said sleeve having, at least at its front end, a lead-in taper to facilitate dilation of said sleeve by said first surface on retraction of said piston.

This arrangement brings a number of significant advantages. The use of a sleeve to carry the annular locking lip results in a structure which can be easily dilated on retraction of the piston to allow the annular retaining projection to engage behind the annular lip, thus reducing the force which need be exerted by the operator. Furthermore, the lead-in taper on the sleeve and the tapered shape of the first surface of the annular retaining projection greatly facilitate the dilation of the sleeve. Although little force is required to draw the annular projection through the sleeve the ultimate connection is strong because of the transverse retaining surface on the annular retaining projection and the inherent rigidity in a longitudinal direction of the sleeve.

With this sort of device it has not proved necessary to take any particular measures to vent the air pocket beneath the piston. This is thought to be due to the sleeve dilating, under the effect of the increased air pressure, sufficiently to allow pressurized air to escape past the annular retaining projection. The complementary surfaces on the annular lip and the annular retaining projection nevertheless define a good secondary blood seal. Blood will in any case not tend to reach this area because it will be trapped in an annular pocket which is advantageously provided at the rear end of the cylindrical tube around the sleeve.

The fact that no special venting features are required, and the fact that the sleeve can be designed so that it has no complicated re-entrant grooves, means that the injection molding required for the blood extracting device can be considerably simplified. Indeed, the various tapers provided for the locking feature are positively beneficial in obtaining release of the injection molded parts from the molding tools. Furthermore, the fact that a sleeve structure is used means that shrinkage problems during injection molding are minimized.

In a preferred embodiment of the invention the annular lip is formed at the rear end of the annular sleeve.

In this arrangement the rear end of the sleeve is conveniently formed as a thin walled conical, or also cylindrical, projection which is separated from the main body of the sleeve by a rearwardly facing undercut. This arrangement further minimizes the effort required on the part of the operator to dilate the sleeve. The arrangement is nevertheless sufficiently rigid that the piston is securely locked to the rear end of the extraction tube.

The lead in taper preferably extends from the front end of the sleeve to the rear end thereof which again minimizes the effort required on the part of the operator and also simplifies the basic injection molding. It is convenient if the angle of this lead-in taper is the same as the taper angle of the first surface of the annular locking projection.

In an alternative embodiment the annular lip can be provided on the sleeve at a position intermediate its front and rear ends. In this arrangement the annular lip can again be disposed remote from the position at which the sleeve is attached to the rear end of the extraction tube; accordingly, the sleeve is not unnecessarily stiff at this location which facilitates the engagement of the annular lip.

In a further embodiment the annular retaining projection is provided on a rearward extension of the piston. This simplifies the form of the piston rod and helps minimize the length of the overall assembly.

In an alternative embodiment the annular retaining projection is provided on the piston rod which can be advantageous because the piston rod is generally made from a harder plastic than the sleeve and piston with the result that the annular retaining projection is more stable and less subject to deformation.

The blood extracting device of the present invention preferably has a front end which is adapted to support a double ended cannula and a plug or seal puncturable by the double ended cannula. In this arrangement the double ended cannula and the plug or seal are usefully carried by a cap screw-threaded onto the front end of the cylindrical body. These arrangements are easy to manipulate and facilitate the extraction of blood from the patient's vein.

The piston rod can be attached to the piston either by a releasable screw thread or simply by providing the piston rod with a weakened portion at which it can be fractured to separate it from the piston.

The arrangement should be such that after removal of the piston rod whether by unscrewing it or by fracturing the piston rod, no part of the piston or piston rod projects beyond the rear end of the cylindrical body. There is then no danger of pressure being exerted on the piston in a forward direction when the cylindrical body is inserted in a centrifuge.

The manufacture of the blood extracting device can be facilitated by manufacturing the structure at the rear end of the cylindrical body as a separate component and subsequently attaching it to the cylindrical body.

Finally, in a particularly preferred arrangement, the internal diameter of the sleeve is at a minimum at the lip and progressively increases to the front and to the rear of the lip. This arrangement facilitates manufacture by injection molding by avoiding re-entrant features.

Figure 4:
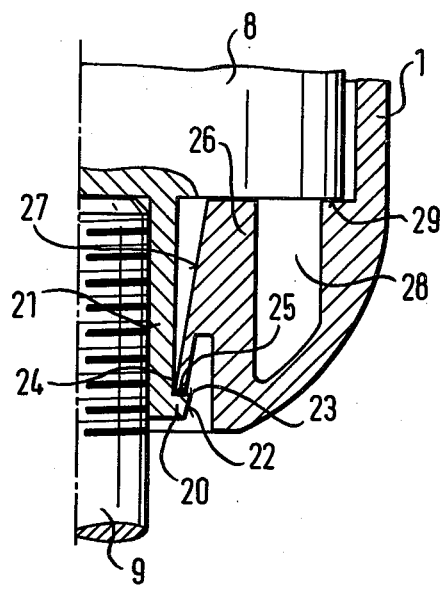
Figure 6:
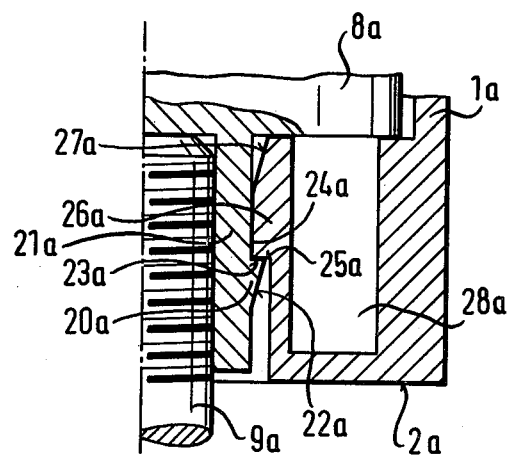
Figure 5:
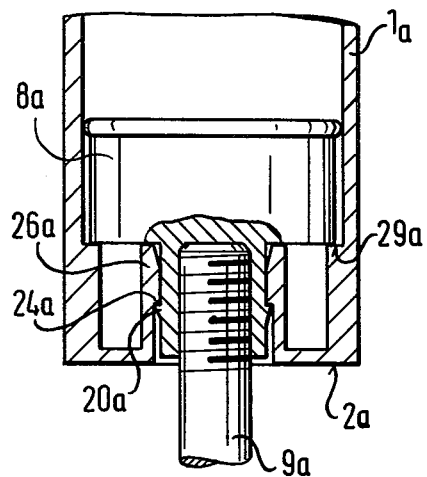
Figure 7:
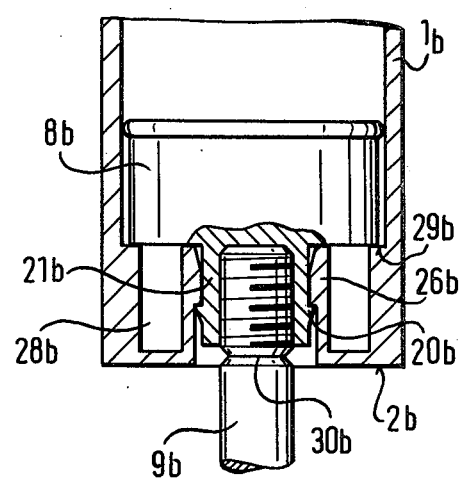
Figure 8:
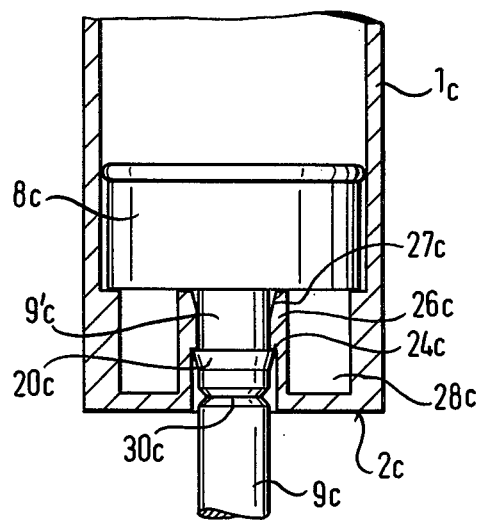

The invention will now be described in further detail by way of example only and with reference to the accompanying drawings which show:

FIG. 1 a side view of a blood extraction and centrifuging device with an attached cannula, FIG. 2 a longitudinal section through the front end of the blood extraction device of FIG. 1 to a larger scale and showing details of the cannula, FIG. 3 a partly sectioned view of the rear end of the blood extraction device of FIG. 1, also to a larger scale, FIG. 4 an enlarged view of part of the drawing of FIG. 3, FIG. 5 a view similar to FIG. 3 but showing an alternative arrangement for the rear end of the blood extraction device, FIG. 6 an enlarged view of part of the arrangement of FIG. 5, FIG. 7 a view similar to that of FIG. 5 but showing a modified embodiment and FIG. 8 a view similar to those of FIGS. 5 and 7 but showing a further modification.

Referring firstly to FIG. 1 there can be seen a blood extraction and centrifuging device having a cylindrical body 1 with a front end 3 and a rear end 2. The front end 3 is adapted to receive a removable cannula 4 which is mounted in a guide sleeve 5 slidably engaged on a projection 6 on a cap 7 which is attached to the front end 3 of the cylindrical body 1 by screw threads. This arrangement will later be described in more detail with reference to FIG. 2.

A piston 8 is sealingly movable in air tight manner within the cylindrical body 1 and a piston rod 9 is removably attached to the piston 8 and extends through a bore 10 at the rear end 2 of the cylindrical body. The piston can be moved by means of the piston rod 9 from an advanced position adjacent the front end 3 to a retracted position adjacent the rear end 2 so as to generate a vacuum in the cylindrical body for extracting blood via the attached cannula 4. Securing means, which will later be described in more detail with reference to FIGS. 3 to 8 are provided for securing the piston to the rear end 2 of the cylindrical body or extraction tube 1.

Two basic modes of operation are possible and will now be briefly described with reference also to FIG. 2.

For the purpose of this discussion it is assumed that the front end of the blood extraction device is provided with a seal such as the rubber plug 11 and foil 12 shown inserted in the neck of the projection 6 in FIG. 2. In the first mode of operation the piston is withdrawn from the fully advanced position to the fully retracted position and is secured in this fully retracted position. As the seal at the front end of the blood extraction device is still intact a partial vacuum is generated in the extraction tube 1. The piston rod 9 can now be separated from the piston 8 or this operation can be left until a later stage. The sharp front end of the cannula 4 is then inserted into a patient's vein. After this has been done the projection 6 is moved into the guide sleeve 5 which causes the sharpened rear end 13 of the double ended cannula 4 to puncture the protective rubber sleeve 14 and subsequently bung 11 and the foil 12. Once the foil 12 has been penetrated the vacuum in the extraction tube 1 is able to suck blood from the patient's vein through the double ended cannula 4. When the extraction tube is full it can be withdrawn from the guide sleeve 5 whereupon the rubber bung seals the front end of the extraction tube and the blood sample contained therein can be inserted into a centrifuge. If the piston rod has not been previously removed it is removed at this stage. Finally the cannular 4 can be withdrawn from the patient's vein. It is also possible to withdraw the cannula 4 from the patient's vein while in position on the tubular body 1.

In the second mode of operation the rubber bung 11 and foil 12 are pierced by the double ended cannula 4 prior to generating a vacuum in the extraction tube 1. In this case it is possible either to insert the cannula into the patient's vein and then effect penetration of the bung and foil or to first assemble the double ended cannula onto the blood extraction device so as to puncture the bung and foil and then to insert the cannula into the patient's vein. The piston can now be retracted very gradually generating a vacuum in the extraction tube 1 so as to extract blood continuously through the cannula 4. This mode of use has the advantage that it can be readily used with very young and very old patients whose veins are liable to collapse if the level of vacuum in the extraction tube 1 is too high. In this mode of use the piston can be retracted either by pulling on the knob 16 or by the use of an automatic retraction device which operates conveniently on the annular bead 17. At the end of the extraction process the piston is once again secured to the rear end 2 of the extraction tube 1 and the piston rod and cannula removed prior to the centrifuging operation.

The detailed construction of the securing means at the rear end of the blood extraction device will now be described with reference to the preferred embodiment shown in FIGS. 3 and 4.

As can be seen from FIGS. 3 and 4 the securing means comprises an annular retaining projection 20 provided at the rear end of a rearwardly directed extension 21 of the piston. The annular retaining projection 20 has a first surface 22 which tapers substantially conically in a rearward direction away from the front end of the extraction tube 1 and a second, retaining surface 23 which extends transverse to the piston rod. The bore 10 at the rear end of the extraction tube 1 is provided with an annular lip 24 which is adapted to snap into engagement behind the annular retaining projection in front of the second, retaining surface 22 as soon as the piston 8 has been sufficiently retracted. The annular lip has a surface 25 complementary to the second retaining surface 23 and is formed on an annular sleeve 26 defining the bore 10. The sleeve 26 has a lead-in taper 27 which facilitates dilation of the sleeve by the first surface 22 on retraction of the piston 8.

In the arrangement of FIGS. 3 and 4 the annular lip 24 is formed at the rear end of the annular sleeve which is constructed as a thin walled conical projection. In a typical embodiment the thickness of this wall would be approximately 0.5 mm which should be compared with a diameter for the extraction tube of approximately 16 mm. The axial length of the thin walled conical projection is conveniently 2 mm.

A conical shape for the projection is preferred but a cylindrical shape can be used if desired. The lead-in taper extends in this embodiment from the front end of the sleeve to the rear end thereof. This is both convenient to manufacture and ensures a progressive dilation of the sleeve during the last phase of retraction of the piston. It will be noted that the sleeve 26 is itself a fairly thin walled structure and this means that it can dilate readily. The sleeve is in fact attached to the rear end 2 of the extraction tube only at its base and cooperates with the extraction tube to form an annular blood trap or groove 28. Blood escaping past the piston 8 during centrifuging operation will collect in this annular blood groove and the air trapped in the space above the blood is able to dissipate through the space defined between the lead in taper 27 and the extension 21 at the rear end of the piston 8. In practice this air is able to escape past the thin wall conical projection of the sleeve without apparent difficulty. In this embodiment the piston rod 9 is attached to the piston by screw threads and can be simply unscrewed. After unscrewing the piston rod no part of the piston projects beyond the rear end of the extraction tube, i.e. removal of the piston rod will in no way affect the security of the connection between the piston and the extraction tube because of the fundamental rigidity of the conically shaped extension. Furthermore, the structure at the rear end of the extraction tube, which is conveniently manufactured separately and attached to a generally tubular body by a welding technique, is readily manufactured using simple tools because of the avoidance of any disturbing re-entrant features.

Turning now to FIGS. 5 and 6 there is shown an alternative embodiment in which the annular lip 24a is provided on the sleeve 26a at a position intermediate its front and rear ends. In this case the lead-in taper 27a does not extend over the full length of the sleeve but is restricted to an initial portion of the sleeve. The remaining features of the annular retaining projection and the annular lip are retained as is indicated by the use of the same reference numerals with the added suffix a. In the embodiment of FIGS. 5 and 6 the piston rod is once again screw fitted into the piston and can be removed simply by unscrewing it.

In the modified embodiment of FIG. 7, in which the same reference numerals are used as previously but with the suffix b, the piston rod 9b is indeed likewise screw-threaded into the extension 21b of the piston but is supplemented by a weak fracture point 30b immediately beneath the thread on the piston rod. In this embodiment the piston rod 9b can be removed simply by snapping it off at the weakened fracture point which significantly simplifies the handling of the blood extraction device.

Reference is finally made to FIG. 8 which shows a further modification in which parts common to the previous figures are again designated with the same reference numerals, but this time with the suffix c.

In the FIG. 8 embodiment the annular retaining projection 20c is provided directly on the piston rod 9c instead of on an extension of the piston 8c. Once again a weak fracture point 30c is provided on the piston rod and indeed immediately below the annular retaining projection 20c. The manner of operation of this device is identical to that of the previous embodiments. The piston rod can either be formed in one piece with the piston head 8c or can be joined to it by any one of a wide variety of known techniques. The latter arrangement is probably preferable because the piston rod can then be made of a harder material and the piston head of a softer material which seals more easily against the walls of the extraction tube.

It will be appreciated by those skilled in the art that various modifications can be made to the described arrangements without departing from the scope of the invention as defined by the appended claims. It is for example possible for the retaining surface of the annular retaining projection to be a shallow conical surface without significantly impairing the effectiveness of the connection between the piston and the rear end of the extraction tube. Indeed, the reliability of this connection may be slightly increased if the retaining surface of the annular retaining projection takes the form of a part conical surface with the notional apex of the cone lying approximately on the axis of the piston rod in a rearward direction. Furthermore, it will be appreciated that a releasable piston rod attached, for example, by screw threads can be re-used with different extraction tubes.

In all embodiments the reference numeral 29 designates an annular shoulder which forms a stop for the piston and restricts its rearward movement.

I claim:

1. A blood extracting and centrifuging device comprising a generally cylindrical body having front and rear ends, said front end being adapted to receive a removable cannula; a piston sealingly movable within said cylindrical body; in a forward direction toward said front end and in a rearward direction toward said rear end; an annular sleeve attached to said rear end of said cylindrical body, said annular sleeve having a central bore; a piston rod attached to said piston, said piston rod having a front end portion adjacent said piston and extending through said bore for moving said piston from an advanced position adjacent said front end to a retracted position adjacent said rear end, whereby to generate a vacuum in said cylindrical body for extracting blood via an attached cannula, means for separating at least a major portion of said piston rod from said piston after movement of the same to said retracted position; and securing means for retaining said piston in said retracted position even after removal of at least said major portion of said piston rod; wherein said securing means comprises a radially outwardly directed, annular, retaining projection on one of a rearwardly directed extension of said piston and said front end portion of said piston rod, and a cooperating, radially inwardly directed, annular lip formed on said annular sleeve; wherein said retaining projection has a first surface, which tapers substantially conically in a rearward direction away from a portion of said projection having an external diameter, and a second, forwardly facing, substantially flat, retaining surface in front of said first surface, said retaining surface extending substantially at right angles to said piston rod; wherein said annular lip has a surface complementary to said retaining surface, has an internal diameter smaller than said external diameter, and is formed on said annular sleeve at a position axially spaced apart from the position at which said sleeve is attached to said rear end of said cylindrical body; wherein said sleeve is provided, at least at its forwardly facing end, with a lead-in taper to facilitate resilient dilation of said sleeve by said first surface on retraction of said piston, whereby to enable said annular lip to snap resiliently into retaining engagement forwardly of said retaining surface on movement of said piston into said retracted position; and wherein no part of said piston or piston rod projects beyond said rear end after separation of at least said major portion of said piston rod from said piston, whereby pressure is not exerted on the piston in a forward direction when the cylindrical body is inserted in a centrifuge.

2. A blood extracting and centrifuging device in accordance with claim 1 and wherein said annular lip is formed at the rear end of said annular sleeve.

3. A blood extracting and centrifuging device in accordance with claim 2 and wherein the rear end of said sleeve is formed as a thin wall conical projection.

4. A blood extracting and centrifuging device in accordance with claim 2 and wherein the annular sleeve is formed as a thin wall cylindrical projection.

5. A blood extracting and centrifuging device in accordance with claim 2 and wherein said lead in taper extends from the front end of said sleeve to the rear end thereof.

6. A blood extracting and centrifuging device in accordance with any one of claims 1 to 5 wherein said annular retaining projection is provided on a rearward extension of said piston.

7. A blood extracting and centrifuging device in accordance with any one of claims 1 to 5 and wherein said annular retaining projection is provided on said piston rod.

8. A blood extracting and centrifuging device in accordance with claim 1 and including means at said front end for supporting a double ended cannula and a sealing plug puncturable by said double ended cannula.

9. A blood extracting and centrifuging device in accordance with claim 8 and wherein said double ended cannula and said sealing plug are carried by a cap screw threaded onto said front end of said cylindrical body.

10. A blood extracting and centrifuging device in accordance with claim 1 and wherein said piston rod is attached to said piston by a releasable screw thread.

11. A blood extracting and centrifuging device in accordance with claim 1 and wherein said piston rod is provided with a weakened portion at which it can be fractured to separate it from said piston.

12. A blood extracting and centrifuging device in accordance with claim 1 and wherein said rear end is of at least part hemispherical shape.

13. A blood extracting and centrifuging device in accordance with claim 1 and wherein the internal diameter of the sleeve is at a minimum at said lip and progressively increases to the front and to the rear of said lip.

14. A blood extracting and centrifuging device comprising a generally cylindrical body having front and rear ends, said front end being adapted to receive a removable cannula; an annular sleeve defining a bore at said rear end; a piston sealingly movable within said cylindrical body in a forward direction toward said front end and in a rearward direction toward said rear end; a piston rod attached to said piston, having a front end portion adjacent said piston and extending rearwardly through said bore for moving said piston from an advanced position adjacent said front end to a retracted position adjacent said rear end, whereby to generate a vacuum in said cylindrical body for extracting blood via an attached cannula; means for removing at least a major portion of said piston rod from said piston after movement of the same to said retracted position; and securing means for retaining said piston in said retracted position even after removal of at least said major portion of said piston rod; wherein said securing means comprises a radially outwardly directed, annular, retaining projection on one of a rearwardly directed extension of said piston and said front end portion of said piston rod, and a cooperating radially inwardly directed annular lip provided on said annular sleeve within said bore; wherein said retaining projection has a first surface, which tapers substantially conically in a rearward direction away from a portion of said projection having an external diameter, and a second, forwardly facing, retaining surface which extends substantially transverse to said piston rod and is located axially forward of said first surface; wherein said annular lip has an internal diameter smaller than said external diameter, and has a surface complementary to said second retaining surface; wherein said sleeve is resilient, has front and rear ends, is attached only by its extreme rear end to said rear end of said cylindrical body at a position spaced rearwardly of said annular lip, and has a lead-in taper, at least at its front end, to facilitate dilation of said sleeve by said first surface on retraction of said piston; wherein said annular lip snaps into a retaining position in front of said retaining surface on movement of said retaining surface rearwardly past said annular lip; and wherein no part of said piston or piston rod projects beyond said extreme rear end after separation of at least said major portion of said piston rod from said piston, whereby pressure is not exerted on the piston in a forward direction when the cylindrical body is inserted in a centrifuge.

15. A blood extracting and centrifuging device in accordance with claim 1 wherein said means for removing comprises a weakened fracture point on the piston rod at a location which, in said retracted position of the piston lies between said annular lip and the extreme rear end of said generally cylindrical body.

16. A blood extracting and centrifuging device comprising a generally cylindrical body having front and rear ends, said front end being adapted to receive a removable cannula; an annular sleeve defining a bore at said rear end; a piston rod attached to said piston, said piston rod having a front end portion adjacent said piston and extending through said bore for moving said piston in a forward direction toward said front end and in a reward direction toward said rear end between an advanced position adjacent said front end to a retracted position adjacent said rear end, whereby to generate a vacuum in said cylindrical body for extracting blood via an attached cannula; securing means comprising a radially outwardly directed, annular, retaining projection on one of a rearwardly directed extension of said piston and said front end portion of said piston rod, and a cooperating radially inwardly directed annular lip provided on said annular sleeve within said bore; wherein said retaining projection has a first surface, which tapers substantially conically in a rearward direction away from a portion of said projection having an external diameter, and a second, forwardly facing, retaining surface which extends substantially transverse to said piston rod and is located axially forward on said first surface; wherein said annular lip has an internal diameter smaller than said external diameter, and has a surface complementary to said second retaining surface; wherein said sleeve is resilient, has front and rear ends, is attached only by one of said ends to a rear portion of said cylindrical body at a position spaced axially from said annular lip, and has a lead-in taper, at least at its front end, to facilitate dilation of said sleeve by said first surface on retraction of said piston, wherein said annular lip snaps into a securing position forwardly of said retaining surface on movement of said retaining surface rearwardly past said annular lip; and wherein the piston rod includes a weakened fracture point which is located so that at least a major portion of said piston rod is removable from said piston rearwardly of said annular projection by breaking it off at a the fracture point, said weakened fracture point lying forwardly of the extreme rear end of said generally cylindrical body, whereby pressure is not exerted on the piston in a forward direction when the cylindrical body is inserted in a centrifuge.

* * * * *